United States Patent [19]

Van Den Elshout et al.

[11] Patent Number: 5,168,110
[45] Date of Patent: Dec. 1, 1992

[54] POWDER COATING BASED ON A CARBOXYL-FUNCTIONAL POLYESTER AND AN EPOXY-FUNCTIONAL CROSS-LINKING AGENT

[75] Inventors: Wilhelmus H. H. A. Van Den Elshout, Sittard; Herman J. Wories, Maastricht; Tosko A. Misev, Zwolle, all of Netherlands

[73] Assignee: DSM N.V. of Het Overloon, Heerlen, Netherlands

[21] Appl. No.: 655,779

[22] Filed: Feb. 15, 1991

[30] Foreign Application Priority Data

Feb. 16, 1990 [NL] Netherlands ............ 9000370
Feb. 16, 1990 [NL] Netherlands ............ 9000371

[51] Int. Cl.$^5$ ............................... C08F 20/00
[52] U.S. Cl. ............................ 525/438; 525/440
[58] Field of Search ..................... 525/438, 440

[56] References Cited

U.S. PATENT DOCUMENTS

| | | | |
|---|---|---|---|
| 3,142,686 | 7/1964 | Kreps et al. ............ | 549/515 |
| 4,087,479 | 5/1978 | Toyota et al. ............ | 525/438 |
| 4,147,737 | 3/1979 | Sein et al. ............ | 525/437 |
| 4,732,853 | 3/1988 | Whitesides et al. ............ | 435/123 |
| 4,801,662 | 1/1989 | Fischer ............ | 525/438 |
| 4,902,756 | 2/1990 | Kordomenos et al. ............ | 525/440 |

FOREIGN PATENT DOCUMENTS

| | | |
|---|---|---|
| 2108217 | 5/1972 | France . |
| 2322172 | 3/1977 | France . |
| 1326669 | 8/1973 | United Kingdom . |

*Primary Examiner*—Melvyn I. Marquis
*Assistant Examiner*—Randy Gulakowski
*Attorney, Agent, or Firm*—Cushman, Darby & Cushman

[57] ABSTRACT

The present invention relates to a powder coating based on a carboxyl-functional polyester and an epoxy-functional cross-linking agent. The cross-linking agent is the reaction product of an isocyanate-containing compound and a hydroxyglycidyl ester. The present invention also relates to the reaction product of a hydroxylglycidyl ester and an isocyanate-containing compound based on an active hydrogen-containing compound and a polyisocyanate. The present invention also relates to hydroxyglycidyl esters with a molecular weight between 132 and 500 and reaction products thereof.

7 Claims, No Drawings

POWDER COATING BASED ON A CARBOXYL-FUNCTIONAL POLYESTER AND AN EPOXY-FUNCTIONAL CROSS-LINKING AGENT

The invention relates to a powder coating based on a carboxyl-functional polyester and an epoxy-functional cross-linking agent. The invention also relates to a hydroxyglycidyl ester, the preparation of this ester and the reaction products of the ester such as the reaction product of the hydroxyglycidyl ester and an isocyanate-containing compound based on a hydroxyl-functional polyester and a polyisocyanate.

The epoxy-functional cross-linking agent used for the preparation of powder coatings based on carboxyl-functional polyesters is often trisglycidylisocyanurate (TGIC). Such a powder coating system is described in U.S. Pat. No. 4,147,737. A disadvantage of the use of TGIC as a cross-linking agent is the possibly mutagenic nature of this compound.

The object of the invention is to provide a cross-linking agent for the preparation of powder coatings based on carboxyl-functional polyesters capable of replacing TGIC.

The invention is characterized in that the cross-linking agent is the reaction product of an isocyanate-containing compound and a hydroxyglycidyl ester with formula (1) or formula (2):

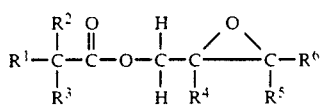

where
$R^1$=OH or a ($C_1$–$C_{20}$) alkyl containing a hydroxyl group,
$R^2$=H or ($C_1$–$C_{10}$) alkyl,
$R^3$=H or ($C_1$–$C_{10}$) alkyl,
$R^4$=H or ($C_1$–$C_4$) alkyl,
$R^5$=H or ($C_1$–$C_4$) alkyl,
$R^6$=H or ($C_1$–$C_4$) alkyl and
where $R^1$ and $R^2$ are jointly capable of forming an aliphatic or aromatic ring containing 4–10 carbon atoms and a hydroxyl group; or

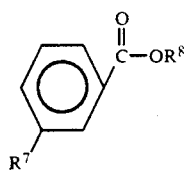

where $R^7$=($C_1$–$C_4$) alkyl with a hydroxyl group, with $R^7$ in the ortho, meta or para position relative to

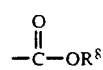

where

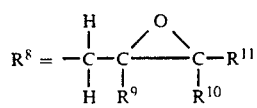

and where
$R^9$=H or $C_1$–$C_4$) alkyl,
$R^{10}$=H or ($C_1$–$C_4$) alkyl and
$R^{11}$=H or ($C_1$–$C_4$) alkyl.

The alkyl group in $R^1$ may be a branched as well as a linear alkyl group.

The alkyl group in $R^1$ may contain another functional group besides the hydroxyl group.

The effect of using the cross-linking agent according to the invention is that TGIC can be replaced, because the desired properties such as glass transition temperature, hardness, impact resistance, flow, thermal stability (no yellowing) and outdoorstability are obtained.

Preferably in formula (1) is:
$R^1$=OH or $CH_2OH$,
$R^2$=($C_1$–$C_4$) alkyl or H,
$R^3$=($C_1$–$C_4$) alkyl or H,
$R^4$=H,
$R^5$=H and
$R^6$=H or $CH_3$.

Preferably, in formula (2) $R^9$=$R^{10}$=H and $R^{11}$=H or $CH_3$.

Preferably, the hydroxyglycidyl ester is the glycidyl ester of hydroxypivalic acid (HPGE), the glycidyl ester of 2-hydroxy-propionic acid, the glycidyl ester of hydroxybutyric acid or the glycidyl ester of 4-hydroxymethylbenzoic acid.

The molecular weight of the hydroxyglycidyl ester is mostly between 132 and 500.

The hydroxyl number of the hydroxyglycidyl ester is mostly between 110 and 424 mg KOH/gramme.

The crosslinking is based on an isocyanate-containing compound. This compound is preferably the reaction product of an active hydrogen-containing compound and at least a polyisocyanate.

Preferably the active hydrogen-containing compound is a hydroxyl-functional compound such as a hydroxyl-functional polyester or a polyol. Other suitable compounds are, for instance, amine-functional compounds.

Suitable hydroxyl-functional polyesters include polyesters with a glass transition temperature between 0° C. and 70° C., a hydroxyl number between 5 and 200 mg KOH/gramme, an acid number lower than 10 mg KOH/gramme and an average functionality of 2 or more.

Suitable polyols include, for instance, trimethylolpropane, trimethylolethane, glycerol, hexanetriol, pentaerythritol, sorbitol and tris-(2-hydroxy)isocyanurate.

Suitable polyisocyanates include, for instance, tetramethylxylylene diisocyanate, 1,6-hexane diisocyanate, 1,5-hexane diisocyanate, 1,5-naphthalene diisocyanate, 4,4'-diphenylmethane diisocyanate, 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, isomers of toluylene diisocyanate, 1-methyl-2,4-diisocyanatecyclohexane, 1,6-diisocyanate-2,2,4-trimethylhexane, 1,6-diisocyanate-2,4,4-trimethylhexane and 1-isocyanatemethyl-3-isocyanate-1,5,5-trimethylcyclohexane (isophorone diisocyanate).

In the preparation of the isocyanate-containing compound the molar ratio between, for instance, the hydroxyl-functional compound and the polyisocyanate is preferably between 0.1:1 and 2:1 mole equivalents. Generally, the reaction temperature is between 30° C. and 200° C., preferably between 80° C. and 150° C., the pressure is between 0.1 10$^5$ Pa and 5 10$^5$ Pa and the reaction time is between 5 minutes and 10 hours, preferably between 30 minutes and 5 hours. Suitable solvents include, for instance, xylene, toluene, hexane, tetrahydrofuran and methylethylketone.

The preparation of the cross-linking agent, effected by reaction of the isocyanate-containing compound and the hydroxyglycidyl ester with formula (1) or formula (2), may take place under the same reaction conditions as described for the preparation of the isocyanate-containing compound, in which process the molar ratio between the hydroxyglycidyl ester and the isocyanate-containing compound is preferably between 0.1:1 and 2:1.

In the past decade, powder coatings have considerably gained in popularity by the ecologically harmless nature, the ease of application and the good quality of these coatings. Very important are the coating systems based on carboxyl-functional polyesters.

The carboxyl-functional polyester resins can be mixed by, extrusion with the cross-linking agent according to the invention, the pigments and the other additives at a temperature of about 90° C.-130° C. and, after electrostatic spraying, they are cured at temperatures between 140° C. and 250° C. under the influence of a customary catalyst. During the curing process, the powder melts and must subsequently flow out to form a smooth, closed coating film before the curing reaction gets on properly.

After the preparation of the carboxyl-functional polyester at temperatures of about 250° C. and the subsequent cooling to 190° C.-200° C., a curing catalyst can be added. The catalyst can be added also during the mixing of the polyester and the cross-linking agent. Preference is given to using the catalyst in amounts of between 0.01% (wt) and 2% (wt) calculated on the carboxyl-functional polyester resin, preferably in amounts of between 0.05 and 1.0% (wt) calculated on the carboxyl-functional polyester resin.

Suitable carboxyl-functional polyesters have an acid number of between 5 and 70, a glass transition temperature of between 30° C. and 90° C. and a hydroxyl number of between 0 and 10.

The carboxyl-functional polyester and the hydroxyl-functional polyester can be obtained via the usual preparation processes from substantially aromatic polycarboxylic acid, such as phthalic acid, isophthalic acid, terephthalic acid, pyromellitic acid, trimellitic acid, 3,6-dichlorophthalic acid, tetrachlorophthalic acid, respectively, in so far as available, the anhydrides, acid chlorides or lower alkyl esters thereof. The carboxylic acid component often consists for at least 50 moles %, preferably at least 70 moles %, of isophthalic acid and/or terephthalic acid.

In addition, the polycarboxylic acids used may be cycloaliphatic and/or acyclic polycarboxylic acid such as, for instance, tetrahydrophthalic acid, hexahydroendomethylenetetra-hydrophthalic acid, azeleic acid, sebacic acid, decanedicarboxylic acid, dimeric fatty acid, adipic acid, succinic acid, maleic acid, in amounts of up to at most 30 moles %, preferably up to a maximum of 20 moles % of the total amount of carboxylic acids. Also, hydroxycarboxylic acids and/or optionally lactones can be used, e.g. 12-hydroxystearic acid, epsilon caprolactone, hydroxypivalic acid ester of neopentyl glycol. In minor amounts monocarboxylic acids, such as benzoic acid, tert.-butylbenzoic acid, hexahydrobenzoic acid and saturated aliphatic monocarboxylic acids can be added also in the preparation.

Furthermore aliphatic diols such as ethylene glycol, propane-1,2-diol, propane-1,3-diol, butane-1,2-diol, butane-1,4-diol, butane-1,3-diol, 2,2-dimethylpropanediol-1,3 (=neopentyl glycol), hexane-2,5-diol, hexane-1,6-diol, 2,2-[bis-(4-hydroxycyclohexyl)]-propane, 1,4-dimethylolcyclohexane, diethylene glycol, dipropylene glycol and 2,2-bis-[4-(2-hydroxylethoxy)]-phenylpropane and smaller amounts of polyols, such as glycerol, hexanetriol, pentaerythritol, sorbitol, trimethylolpropane and tris-(2-hydroxy)-isocyanurate can be used. Instead of diols, respectively polyols, it is possible also to use epoxy compounds. The alcohol component preferably contains at least 50 moles % neopentyl glycol and/or propylene glycol.

The carboxyl-functional polyesters are prepared via processes known per se, by esterification or re-esterification, optionally in the presence of customary catalysts such as, for instance, dibutyltin oxide or tetrabutyl titanate, in which processes, owing to a proper choice of the preparation conditions and of the COOH/OH ratio, end products with acid numbers between 5 and 150 are obtained.

Of course, customary additives such as for example pigments, fillers, flow agents and stabilizers can be added to the coating systems. Suitable pigments are, for instance, inorganic pigments such as titanium dioxide, zinc sulphide, iron oxide and chromium oxide and organic pigments, such as azo compounds. Suitable fillers include, for instance, metal oxides, silicates, carbonates and sulphates.

The invention also relates to hydroxylglycidyl esters with a molecular weight between 132 and 500 and reaction products thereof.

The process for preparation of hydroxyglycidyl esters according to the invention is characterized in that in a first step a hydroxy acid or hydroxyalkyl ester is saponified with lye, and in a second step the product obtained in the first step is reacted with epichlorohydrin.

The reaction temperature in the first step is between 30° C. and 200° C. and in the second step between 30° C. and 150° C. The pressure in the first step is between $10^3$ Pa and $10^6$ Pa and in the second step between $10^2$ Pa and $10^6$ Pa. The reaction time in the first step is between 5 minutes and 5 hours and in the second step between 1 minute and 5 hours.

Hydroxypivalic acid, hydroxyisobutyric acid, 2-hydroxypropionic acid and/or p-methylolbenzoic acid are preferably used as hydroxy acids in the first step.

Hydroxypivalic methylester is preferably used as hydroxyalkyl ester in the first step.

Sodium hydroxide is preferably used as lye.

The molar ratio lye:hydroxy acid or hydroxyalkyl ester is between 0.5:1 and 1.5:1 and the molar ratio epichlorohydrin:hydroxy acid or hydroxyalkyl ester is between 1:1 and 10:1.

Suitable solvents used in the first step include, for instance, xylene, toluene and/or water.

Besides this two-step synthesis, the hydroxyglycidyl esters may also be prepared via a one-step synthesis by mixing hydroxy acid and/or hydroxyalkyl ester, lye and epichlorohydrin at temperatures between 30° C. and 200° C.

The invention also relates to the reaction product of a hydroxyglycidyl ester according to the invention and an isocyanate containing compound. Suitable isocyanate containing compounds are for instance aliphatic, cycloaliphatic and aromatic di-, tri- and tetraisocyanates, such as for example 1,5-naphthalene diisocyanate, 4,4'-diphenylmethane diisocyanate, 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, isomers of toluene diisocyanate, 1-methyl-2,4-diisocyanate cyclohexane, 1,6-diisocyanate-2,2,4-trimethyl hexane and 1-isocyanatemethyl-3-isocyanate-1,5,5-trimethyl cyclohexane, chlorinated and brominated diisocyanates, phosphorus containing diisocyanates, isoforon diisocyanate, 4.4'-diisocyanate phenylperfluoroethane, tetramethoxy, 1.4'diisocyanate, butane 1.4-, hexane-1,5-diisocyanate, hexane 1.6-diisocyanate, dicyclohexylmethane diisocyanate, cyclohexane 1.4-diisocyanate, ethylene diisocyanate, phthalic acid-bis-isocyanate ethyl 1-chloromethylphenyl 2.4-diisocyanate, 1-bromomethylphenyl 2.6-diisocyanate, 3.3-bis-chloromethyl ether 4.4'-diphenyl diisocyanate, tetramethylxylylene diisocyanate, isocyanate-groups-containing adducts and isocyanurates of the above-mentioned diisocyanates.

The invention also relates to the reaction product of a hydroxyl functional and/or amine functional compound, a polyisocyanate and a hydroxyglycidyl ester according to the invention.

Suitable amine functional compounds include, for instance, ethylenediamine, propylenediamine, ethanolamine, propanolamine, butylenediamine, pentamethylenediamine, hexamethylenediamine, decamethylenediamine, 4,7-dioxadecane-1, 10-diamine, dodecamethylenediamine, 4,9-dioxadodecane-1, 12-diamine, 7-methyl-4, 10-dioxatridecane-1,13-diamine, 1,2-diaminocyclohexane, 1,4-diaminocyclohexane, 4,4'-diaminodicyclohexylmethane, isoforondiamine, bis-(3-methyl-4-aminocyclohexyl)methane, 2,2-bis-(4-aminocyclohexyl)propane, nitrile tris(ethane amine), polyetherpolyamine, bis-(3-aminopropyl)methylamine, 3-amino-1-(methylamine)propane, 3-amino-1-(cyclohexylamino)propane, N-(2-hydroxyethyl)ethylenediamine, polypropoxylenedi-/triamines and polyethoxylenedi triamines.

Suitable hydroxyl functional compounds are for instance polyols and hydroxyl functional polymers.

Suitable polyols are for instance aliphatic diols, such as ethylene glycol, propane-1,2-diol, propane-1,3-diol, butane-1,2-diol, butane-1,4-diol, butane-1,3-diol, 2,2-dimethylpropanediol-1,3 (=neopentyl glycol), hexane-2,5-diol, hexane-1,6-diol, 2,2-[bis-(hydroxycyclohexyl)]-propane, 1,4-dimethylolcyclohexane, diethylene glycol, d-ipropylene glycol and 2,2-bis-[4-(2-hydroxyethoxy)]-phenylpropane and polyols, such as glycerol, hexanetriol, pentaerytritol, sorbitol, trimethylolethane, trimethylolpropane and tris-(2-hydroxy)-isocyanurate.

Suitable hydroxyl functional polymers include, for instance, hydroxyl functional polyesters, hydroxyl functional polyurethanes, hydroxyalkyl(meth)acrylate polymers, vinylalcohol acetate copolymers and allylalcohol copolymers.

Suitable hydroxyl functional polyesters are for instance polyesters having a hydroxyl number between 5 and 200 mg KOH/g, an acid number lower than 10 mg KOH/g and an average functionality of 2 or more.

The hydroxyl functional polyesters can be obtained via customary methods of preparation from polycarboxylic acids, such as for instance adipic acid, sebacic acid, phthalic acid, isophthalic acid, terephthalic acid, pyromellitic acid, trimellitic acid. 3,6-dichlorophthalic acid, tetrachlorophthalic acid or, respectively, in so far as to be obtained, the anhydrides, acid chlorides or lower alkyl esters thereof, and from aliphatic diols, such as for instance ethylene glycol, propane-1,2-diol, propane-1,3-diol, butane-1,2-diol, butane-1,4-diol, butane-1,3-diol, 2,2-dimethylpropanediol-1,3 (=neopentylglycol), hexane-2,5-diol, hexane-1,6-diol, 2,2-[bis-(hydroxycyclohexyl)]-propane, 1,4-dimethylolcyclohexane, diethylene glycol, dipropylene glycol and 2,2-bis-4-(2-hydroxyethoxy)]-phenylpropane and minor quantities of polyols, such as glycerol, hexanetriol, pentaerytritol, sorbitol, trimethylolethane, trimethylolpropane and tris-(2-hydroxy)-isocyanurate. Further, fatty acids may be used, such as for instance linseed oil and soya oil.

Suitable hydroxyl functional poyurethanes include for instance polyurethanes based on aliphatic, cycloaliphatic and aromatic di-, tri- and tetraisocyanates, such as for example 1,5-naphthalene diisocyanate, 4,4'-diphenylmethane diisocyanate, 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, isomers of toluene diisocyanate, 1-methyl-2,4-diisocyanate cyclohexane, 1,6-diisocyanate-2,2,4-trimethyl hexane and 1-isocyanatemethyl-3-isocyanate-1,5,5-trimethyl cyclohexane, chlorinated and brominated diisocyanates, phosphorus containing diisocyanates, isoforon diisocyanate, 4.4'-diisocyanate phenylperfluoroethane, tetramethoxy, 1.4'diisocyanate, butane 1.4-, hexane-1,5-diisocyanate, hexane 1.6-diisocyanate, dicyclohexylmethane diisocyanate, cyclohexane 1.4-diisocyanate, ethylene diisocyanate, phthalic acid-bisisocyanate ethyl ester, 1-chloromethylphenyl 2.4-diisocyanate, 1-bromomethylphenyl 2.6-diisocyanate, 3.3-bis-chloromethyl ether 4.4'-diphenyl diisocyanate, tetramethylxylylene diisocyanate, isocyanate-groups-containing adducts and isocyanurates of the above-mentioned diisocyanates, and on polyols such as for instance trimethylolpropane, trimethylolethane, cyclohexanedimethanol, 1,6-hexanediol, hexane-2,5-diol, neopentylglycol, ethyleneglycol, diethyleneglycol, propyleneglycol, 1,2-butanediol, 1,3-butanediol 1,4-butanediol, (di)sorbitol, (di)pentaerytritol, trishydroxyethylisocyanurate, glycerol, polypropyleneglycol, polyethyleneglycol and polytetrahydrofuran.

Suitable hydroxyalkyl(meth)acrylate polymers include, for instance, hydroxyethyl(meth)acrylates and hydroxypropyl(meth)acrylate As comonomers, these acrylate polymers may contain for instance acrylate monomers, styrene monomers, vinyl monomers, ethene propene monomers, allyl monomers and acrylonitrile monomers.

Suitable polyisocyanates include, for instance, 1,6-hexane diisocyanate, 1,5-hexane diisocyanate, 1,5-naphthalene diisocyanate, 4,4'-diphenylmethane diisocyanate, 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, isomers of toluene diisocyanate, 1-methyl-2,4-diisocyanate cyclohexane, 1,6-diisocyanate-2,2,4-trimethyl hexane, 1,6-diisocyanate-2,2,4-trimethyl hexane and/or 1-isocyanatemethyl-3-isocyanatetrimethyl-1,5,5-cyclohexane (isophorone diisocyanaat). The reaction product of a hydroxyl functional and/or amine functional compound, a polyisocyanate and the hydroxyglycidyl ester according to the invention can be prepared by addition in arbitrary sequence and quantities. Preferably, the molar ratio between the hydroxyl functional polymer and/or amine functional polymer and the polyisocyanate is between 0.1:1 and 2:1 mole equivalents. The reaction temperature is generally between 30° C. and 200° C., preferably between 80° C. and 150° C., the pressure between $0.1.10^5$ Pa and $5.10^5$ Pa, and the reaction time between 5 minutes and 10 hours, preferably between 30 minutes and 5 hours. Suitable solvents include, for instance, xylene, toluene, tetrahydroxyfuran, hexane, dichloro(m)ethane and methylethylketone.

The reaction product of the hydroxylglycidyl ester according to the invention and the isocyanate containing compound can be cured with aliphatic and aromatic polyamines, aliphatic and aromatic polyacids, polyamides, polyaminoamides, polyaminourethanes, acid polyesters, acid polyacrylates, imidazoles, mercaptanes, phenols, silanes, acetoacetates, polyurea, polyisocyantes, oxazolidones and melamine resins. The reaction product can also be cured, with use of customary catalysts for epoxy resins, without addition of a crosslinking agent.

The reaction products according to the invention can be mixed with customary compounds containing epoxy groups, such as for instance diglycidyl ethers of bisphenol A and TGIC.

The reaction products according to the invention can also be used as binding agents in for instance coatings, such as water- or solvent-based coating systems, but they can also be used in, for instance, adhesives, construction materials, electrical and electronic materials, foams and inks.

Suitable substrates for the powdercoatings and water- or solvent based coatings include, for example, plastics, wood, metal and glass.

The invention will now be further elucidated by means of the following examples, and comparative experiments without however being restricted thereto.

EXAMPLE I

Preparation of hydroxypivalic glycidyl ester 132 parts by wt. (1 mole) hydroxypivalic methyl ester, 48 parts by wt. (1.2 mole) sodium hydroxide solution and 250 ml water were heated for 1 hour at 100° C. in a 0.5-liter three-neck flask equipped with stirrer, thermometer and reflux cooler. The temperature was reduced to 50° C. To the mixture were added 276 parts by wt. (3 mole) epichlorohydrin (ECH) and 50 parts by wt. Dowex (Fluka AG, 1×8). The water was removed azeotropically at a temperature of 50° C. and at reduced pressure (200 mbar), the ECH being supplied back to the reaction mixture. The total reaction time was 3 hours. The salt formed was filtered off and washed twice with 20 ml ECH The excess ECH was removed by means of rotary film evaporation. Thus 167 parts by wt. hydroxypivalic glycidyl ester were obtained in the form of a light yellow liquid with an epoxide content of 5.5 meq/g and a hydroxy content of 307 mg KOH/g.

EXAMPLE II

Preparation of hydroxypivalic glycidyl ester 96 parts by wt. 50% sodium hydroxide solution (in water) were added dropwise in 1 hour to 118 parts by wt. (1 1 mole) hydroxypivalic acid and 200 ml xylene, the temperature of the reaction mixture being kept at 110° C. The whole was kept at 110° C. for half an hour. After cooling to 50° C., 276 parts by wt. (3 mole) epichlorohydrin and 50 g Dowex were added to the reaction mixture. The temperature of the reaction mixture rose to 105° C. At this temperature the mixture was afterreacted for 1 hour. After cooling to 50° C. the water was removed azeotropically at reduced pressure (200 mbar). The salt formed and the Dowex were filtered off. The residue was washed twice with 20 ml ECH. The entire organic phase (ECH+xylene) was removed by means of rotary film evaporation. Thus 160 parts by wt. hydroxypivalic glycidyl ester were obtained in the form of a light yellow liquid with an epoxide content of 5.6 meq/g and a hydroxy content of 310 mg KOH/g.

EXAMPLE III

Preparation of a hydroxyfunctional polyester

In a 2-liter three-neck flask, equipped with stirrer, thermometer and reflux cooler, 498 parts by weight (3 mole) isophthalic acid and 416 parts by weight neopentylglycol were heated to 225° C. The reaction mixture was kept at this temperature for 12 hours. The reaction water was removed by distillation. After cooling a (white) hydroxyfunctional polyester resin was obtained with a hydroxy content of 118 mg KOH/g, an acid number of <1 mg KOH/g and a Tg of 25° C.

EXAMPLE IV

Preparation of an epoxy functional crosslinking agent 22.9 parts by wt. isoforon diisocyanate and 0.1 part by wt. dibutyl tin laurate were added to 50 parts by wt. polyester obtained according to Example III, and 200 ml xylene. The reaction mixture was kept at 110° C. for 1 hour. Next, 18.5 parts by wt. of the hydroxypivalic glycidyl ester obtained according to Example II were added dropwise to the reaction mixture in half an hour. The temperature was kept at 130° C. for 1 hour. The organic solvent was removed by means of rotary film evaporation. The product thus obtained was a light yellow solid substance with an epoxy content of 1.1 meq/g and a Tg of 35° C.

It is highly unexpected for the Tg of this reaction product not to be much lower than of the starting polyester. The fact is that extension of the polymer chain with an isocyanate compound often results in a lowering of the Tg. Particularly for the use in powder coatings, where the Tg must be such that at room temperature a stable system is obtained, the phenomenon observed is a great advantage.

EXAMPLE V

Preparation of powder coating based on a carboxyl-functional polyester and a cross-linking agent according to Example IV 391 parts by weight of a carboxylic acid-terminated polyester (Uralac P 3500 TM; DSM Resins B.V.) with an acid number of 30 mg KOH/g is mixed in an extruder (Werner & Pfleiderer, ZSK 30) at 120° C. with 209 parts by weight cross-linking agent (obtained according to Example IV), with 400 parts by weight titanium dioxide pigment (Kronos CL 310 TM), with 9 parts by weight flow agent (Resiflow PV-5, Worle) and with 4.5 parts by weight benzoin. Ater cooling, the extrudate is reduced in size, pulverized and screened to a particle size of 90 μm. The powder has a Tg of 40° C.

EXAMPLE VI

Preparation of a cross-linking agent based on TMP, IPDI and HPGE

In a flask (two liters), provided with stirrer, thermocouple and reflux condenser, 120.6 parts by weight trimethylolpropane (TMP), 603.8 parts by weight isophorone diisocyanate (IPDI), 948 parts by weight toluene and 1.78 parts by weight dibutyltin dilaurate were put together. The flask was heated to 50° C.

Subsequently, an exothermic reaction occurred in which the temperature rose to 85° C. After 30 minutes, the isocyanate number was 6.85%. Subsequently, within 5 minutes of the colourless, clear mixture being cooled to 50° C., 475.0 parts by weight HPGE was added. The temperature rose to 65° C.; after 30 minutes no isocyanate could be demonstrated any more via infrared analysis.

Finally, the toluene was drained off under vacuum. The weight of an epoxy equivalent (WPE) was 447. The resulting product was colourless and had a glass transition temperature of 33° C.

EXAMPLE VII

Preparation of powder coating 470 parts by weight of a carboxylic acid-terminated polyester (Uralac P DSM Resins B.V.) with an acid number of 30 mg KOH/g was mixed in an extruder (Werner & Pfleiderer, ZSK 30) at 120° C. with 130 parts by weight cross-linking agent according to Example VI, with 400 parts by weight titanium dioxide pigment (Kronos CL 2160 TM), with 9 parts by weight flow agent (Resiflow PV-5, Worle) and with 4.5 parts by weight benzoin. After cooling, the extrudate was reduced in size, pulverized and screened to a particle size of 90 μm. The resulting powder had a Tg of 40° C. The reverse impact of a coating (with a coating thickness of 50 μm) was 160 μm poundinch.

This property was obtained after curing for 10 minutes at 200° C.

COMPARATIVE EXPERIMENT A

Preparation of a powder coating based on a carboxyl-functional polyester and a cross-linking agent according to Example IV 558 parts by weight of a carboxylic acid-terminated polyester (Uralac P 3500 TM; DSM Resins B.V.) with an acid number of 30 mg KOH/g was mixed in an extruder (Werner & Pfleiderer, ZSK 30) at 120° C. with 42 parts by weight TGIC, with 400 parts by weight titanium dioxide pigment (Kronos 2160 TM), with 9 parts by weight flow agent (Resiflow PV-5, Worle) and with 4.5 parts by weight benzoin. After cooling, the extrudate was reduced in size, pulverized and screened to a particle size of 90 μm. The powder had a Tg of 40° C. The reverse impact of a coating (with a coating thickness of 50 μm) was 160 poundinch. This property was obtained after curing for 10 minutes at 200° C.

EXAMPLE VIII

Mutagenicity test

In order to determine the mutagenicity, the procedures were followed as laid down in the directives of the OECD (directive 471: 'Genetic Toxicology: Salmonella typhimurium Reverse Mutation Assay' (adopted 26.05.1983)) and the EEC (directive 84/449/EEC—Annex V of EEC directive 67/548/EEC, Part B: Methods for Determination of Toxicity; B14: ‚Other effects—Mutagenicity: *Salmonella typhimurium*—Reverse Mutation Assay, EEC Publication L 251 (adopted 19.09.1984)). The objective of this study is to evaluate the testsubstance for its capability to induce 'reverse mutations' in a gene of a histidine-requiring *Salmonella typhimurium* bacterial strains to produce histidine-independent strains of these micro-organism.

The tests revealed that TGIC (3330) showed mutagenic activity in both strain TA 98 and strain TA 100, whereas the cross-linking agent according to Example IV showed no mutagenic activity in these strains.

EXAMPLE IX

Preparation of a coating on the basis of the crosslinking agent obtained in accordance with Example VI 84.5 parts by wt. of a carboxylic acid terminated polyester (P 3500 TM, DSM Resins B.V.) with an acid number of 37.3 mg KOH/g were mixed with 28.1 parts by wt. crosslinking agent according to Example VI and 100 parts by wt. toluene.

The coating obtained had a reverse impact (at a layer thickness of 50 μm) of 160 poundinch. This property was obtained after curing for 6 minutes at 200° C.

We claim:

1. Powder coating based on a carboxyl-functional polyester and an epoxy-functional cross-linking agent, characterized in that the cross-linking agent is the reaction product of an isocyanate-containing compound and a hydroxyglycidyl ester with formula (1) or formula (2):

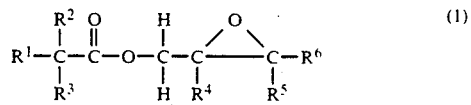

(1)

where
R$^1$ = OH or a (C$_1$–C$_{20}$) alkyl containing a hydroxyl group,
R$^2$ = H or (C$_1$–C$_{10}$) alkyl,
R$^3$ = H or (C$_1$–C$_{10}$) alkyl,
R$^4$ = H or (C$_1$–C$_4$) alkyl,
R$^5$ = H or (C$_1$–C$_4$) alkyl,
R$^6$ = H or (C$_1$–C$_4$) alkyl and
where R$^1$ and R$^2$ are jointly capable of forming an aliphatic or aromatic ring containing 4–10 carbon atoms and a hydroxyl group; or

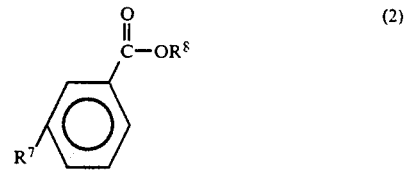

(2)

where R$^7$ = (C$_1$–C$_4$) alkyl with a hydroxyl group, with R$^7$ in at the ortho, meta or para position relative to

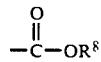

where

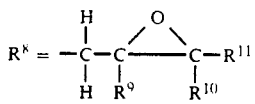

and where
$R^9$=H or $(C_1-C_4)$ alkyl
$R^{10}$=H or $(C_1-C_4)$ alkyl and
$R^{11}$=H or $(C_1-C_4)$ alkyl.

2. Powder coating according to claim 1, characterized in that
$R^1$=OH or $CH_2OH$,
$R^2$=$(C_1-C_4)$ alkyl or H,
$R^3$=$(C_1-C_4)$ alkyl or H,
$R^4$=H,
$R^5$=H and
$R^6$=H or $CH_3$.

3. Powder coating according to claim 1, characterized in that the hydroxyglycidyl ester is the glycidyl ester of hydroxypivalic acid, the glycidyl ester of 2-hydroxypropionic acid, the glycidyl ester of hydroxybutyric acid or the glycidyl ester of 4-hydroxymethylbenzoic acid.

4. Powder coating according to claim 1, characterized in that the isocyanate-containing compound is the reaction product of an active hydrogen-containing compound and at least a polyisocyanate.

5. Powder coating according to claim 4, characterized in that the active hydrogen-containing compound is a hydroxyl-functional compound.

6. A coating composition comprising the powder coating according to claim 1.

7. Wholly or partly coated substrate, characterized in that the coating material comprises a powder coating according to claim 1.

* * * * *